United States Patent
Landau

(10) Patent No.: US 6,572,581 B1
(45) Date of Patent: Jun. 3, 2003

(54) ERGONOMIC NEEDLE-LESS JET INJECTION APPARATUS AND METHOD

(75) Inventor: Sergio Landau, Laguna Nigel, CA (US)

(73) Assignee: Bioject Inc., Portland, OR (US)

( * ) Notice: Subject to any disclaimer, the term of this patent is extended or adjusted under 35 U.S.C. 154(b) by 144 days.

(21) Appl. No.: 09/588,279

(22) Filed: Jun. 5, 2000

Related U.S. Application Data

(63) Continuation-in-part of application No. 09/252,131, filed on Feb. 18, 1999, now Pat. No. 6,264,629.

(51) Int. Cl.[7] .................................................. A61M 5/30
(52) U.S. Cl. ............................ 604/68; 604/69; 604/143
(58) Field of Search ..................... 604/68–72, 131–136, 604/140–143, 414, 218

(56) References Cited

U.S. PATENT DOCUMENTS

| | | | | |
|---|---|---|---|---|
| 3,688,765 A | * | 9/1972 | Gasaway ..................... 604/70 |
| 4,790,824 A | * | 12/1988 | Morrow et al. ............. 604/143 |
| 5,009,637 A | * | 4/1991 | Newman et al. .............. 604/68 |
| 5,334,144 A | * | 8/1994 | Alchas et al. ................. 604/68 |
| 5,499,972 A | * | 3/1996 | Parsons ....................... 604/68 |
| 5,704,911 A | * | 1/1998 | Parsons ....................... 604/68 |
| 5,769,138 A | * | 6/1998 | Sadowski et al. ........... 604/414 |
| 5,865,795 A | * | 2/1999 | Schiff et al. .................. 604/70 |
| 5,911,703 A | * | 6/1999 | Slate et al. ................... 604/68 |
| 5,921,967 A | * | 7/1999 | Sadowski et al. .......... 604/218 |
| 5,938,637 A | * | 8/1999 | Austin et al. ................. 604/68 |
| 6,053,890 A | * | 4/2000 | Moreau Defarges et al. . 604/68 |
| 6,080,130 A | * | 6/2000 | Castellano .................... 604/68 |
| 6,096,002 A | * | 8/2000 | Landau ......................... 604/68 |
| 6,210,359 B1 | * | 4/2001 | Patel et al. .................... 604/68 |
| 2001/0051789 A1 | * | 12/2001 | Parsons ....................... 604/68 |

* cited by examiner

Primary Examiner—Thomas Denion
Assistant Examiner—Thai-Ba Trieu
(74) Attorney, Agent, or Firm—Kolisch Hartwell, P.C.

(57) ABSTRACT

A gas-powered, single-use, needle-less jet injection device (10, 210, 410) includes a hand-held injector (12, 212, 412), and a drug injection cartridge (14, 114, 414) which provides a volume of liquid medication to be injected, an injection orifice, and an injection piston. Forceful movement of the injection piston causes an injection jet of medication to be expelled from the injection orifice. The injection device also includes a hermetically sealed gas pressure cartridge (82, 182, 382) which remains sealed until the moment of injection and powers the jet injection after opening of this cartridge.

22 Claims, 7 Drawing Sheets

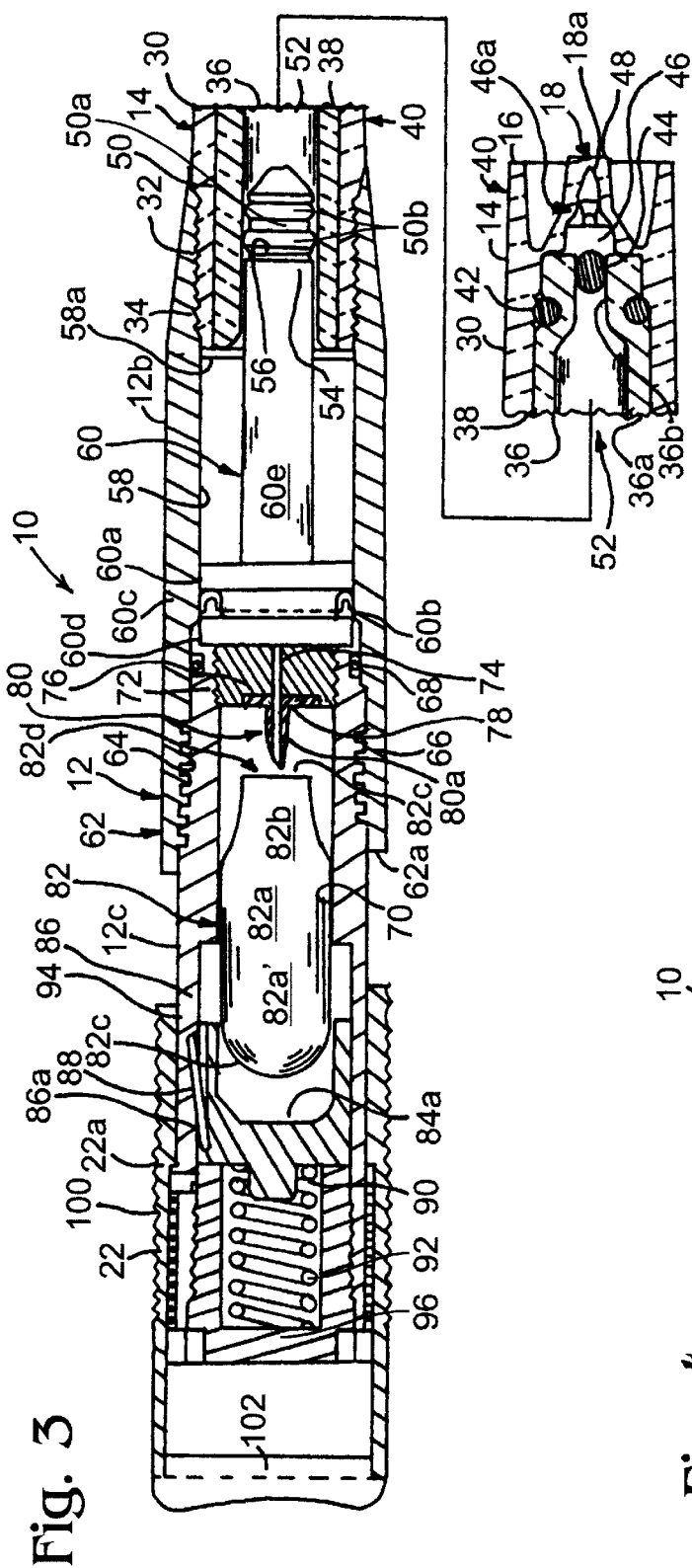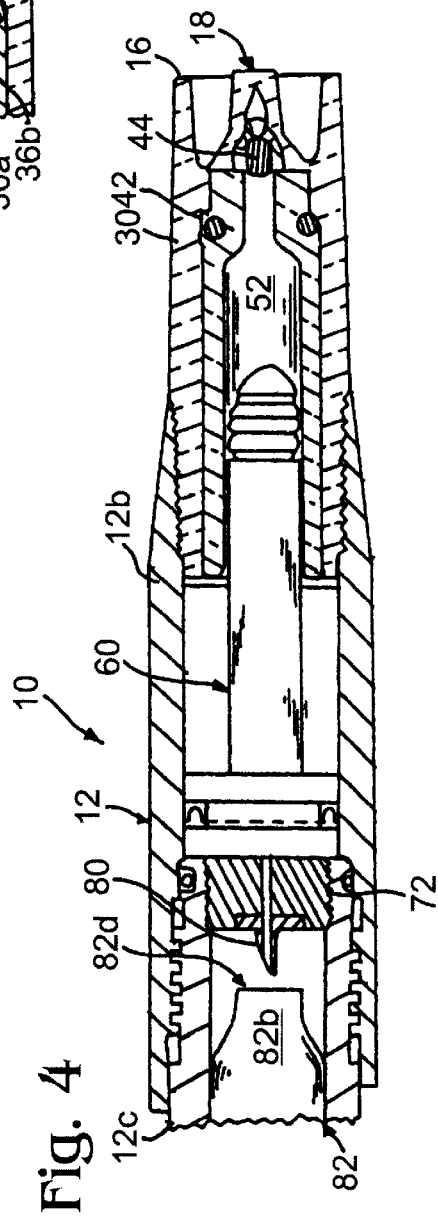
Fig. 3
Fig. 4

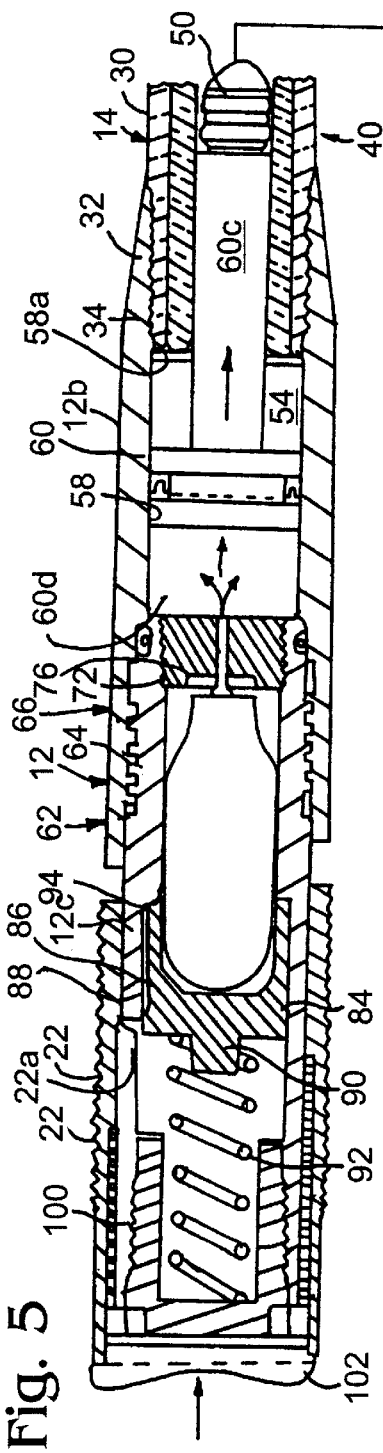
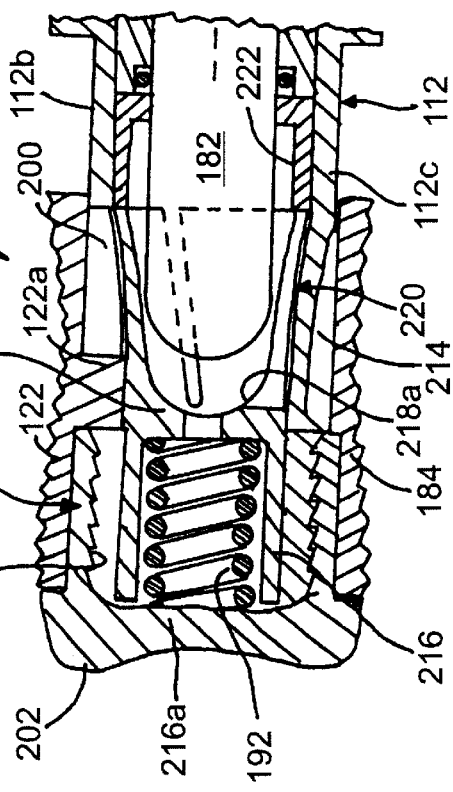
Fig. 5
Fig. 6

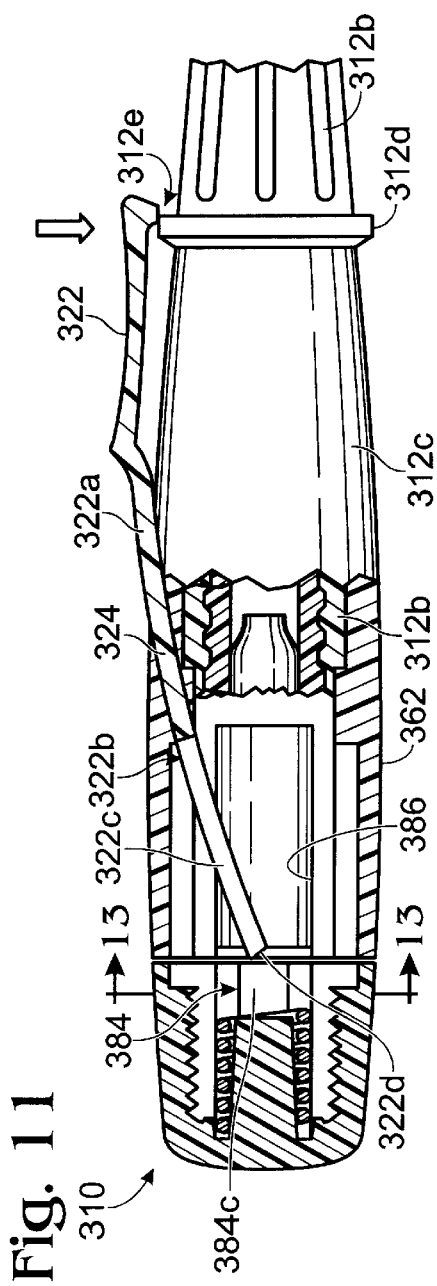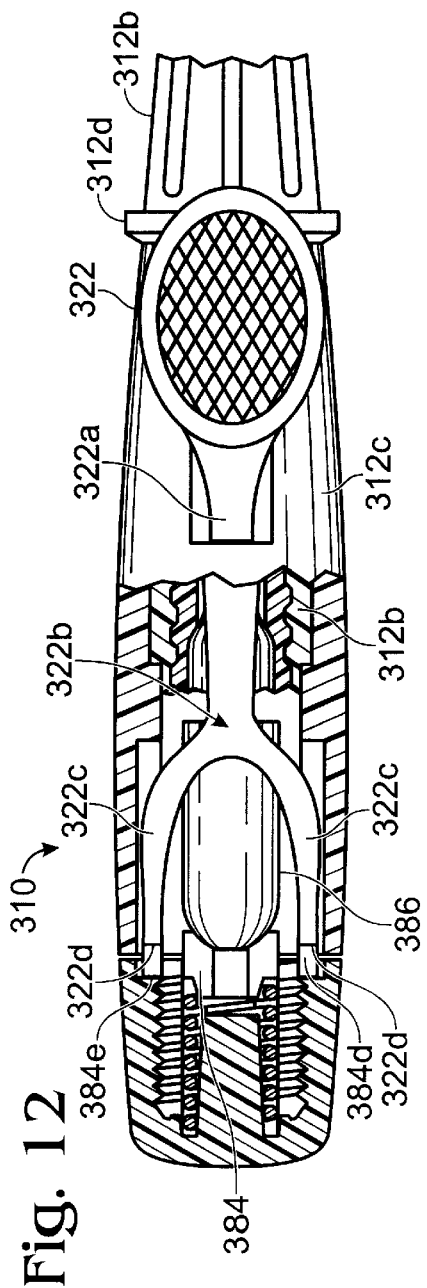

ERGONOMIC NEEDLE-LESS JET INJECTION APPARATUS AND METHOD

CROSS REFERENCE TO RELATED APPLICATION

This application is a Continuation-in-Part of U.S. patent application, Ser. No. 09/252,131, filed Feb. 18, 1999, Now U.S. Pat. No. 6,264,629.

BACKGROUND OF THE INVENTION

1. Field of the Invention

The present invention relates generally to a single-use disposable needle-less (or needle-free) jet injection device. Particularly, this invention relates to an ergonomic jet injection device which comprises a hand-held injector having a pre-filled drug cartridge sealingly carrying injectable medication, a sealed cylinder of pressurized gas, a pre-energized discharge mechanism for penetrating the gas cylinder, and a trigger device for releasing the discharge mechanism. Features are provided which simultaneously unseal the drug cartridge and prepare the device for performing a jet injection when a user of the device changes it from a storage configuration to a use configuration. A safety feature prevents an accidental jet injection. When the user actuates the injection device, the trigger device releases the discharge mechanism to penetrate the gas cylinder, which drives a piston of the drug cartridge to effect a jet injection.

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued Jun. 24, 1986 to J. Thomas Morrow, et al.; U.S. Pat. No. 4,913,699; issued Apr. 3, 1990 to James S. Parsons; and U.S. Pat. No. 5,730,723, issued Mar. 24, 1998, to Thomas P. Castellano, et al. WIPO publication WO 97/37705 also discloses a gas powered disposable needle-less hypodermic jet injector.

The Morrow, et. al. '556 patent is believed to teach a reusable hypodermic jet injection device in which a housing receives a shell or cartridge having a bore leading to a discharge aperture. Within the bore is received both a plunger sealingly engaging the bore, and a ressurized gas cylinder which rests against the plunger. The injection device includes a ram which has a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger, and spent gas cylinder, is discarded after an injection; and a new shell pre-filled with medication and with a new gas cylinder is used for each injection.

The Parsons '699 patent is believed to teach a single-use jet injector which is totally discarded after one use. This jet injector is believed to have a body with a pair of gas chambers separated by a breakable valve. One of the gas chambers contains a pressurized gas, while the other chamber is sealingly bounded by a piston which drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thomlea, is believed to disclose a disposable hypodermic jet injector in which the device is powered by a gas pressure spring of the type common in the tool and die art as a substitute for the conventional metal spring-powered ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice in order to produce a jet hypodermic injection from liquid held in the bore ahead of the piston.

The Weston device is thought to have several deficiencies: such as difficult and costly manufacturing and sterilization processes, because pressurized gas and a drug dose need to be contained in the same package; and including a possible inability to endure long-term storage while still retaining the gas pressure in the gas spring to power an injection, and also maintaining the medication integrity. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

SUMMARY OF THE INVENTION

In view of the above, it is desirable and is an object for this invention to provide a needle-less jet injection device which reduces the severity of or avoids one or more of the limitations of the conventional technology.

Thus, it is an object of this invention to provide a particularly ergonomic single-use, disposable, needle-free gas-powered jet injector utilizing a pressurized gas source which is hermetically sealed until the moment of injection.

Further, an object of this invention is to provide such an ergonomic gas powered jet injector in which the device has a storage configuration and a use configuration. In the storage configuration, the device is safe, with the drug cartridge sealed closed, and is incapable of effecting a jet injection. In the use configuration, the device is prepared for making a jet injection, with the drug cartridge opened in preparation for this injection.

Additionally, an object for this invention is to provide such an injection device having a multi-function component which alternatively maintains the injector in a safe storage condition, and also allows a user to place the injection device into a use condition preparatory for performing a jet injection. When the user placed the device into the use configuration, the multi-function component prepares the jet injection device by effecting unsealing of the previously sealed drug cartridge, and also removes a safety block from an obstructing position relative to a trigger of the device. Thereafter, the thumb pad trigger of the injector can be manually activated by a user of the device to perform an injection.

Accordingly, an ergonomic needle-less jet injection system embodying this invention includes, for example: an elongate generally cylindrical device body having a forward end; a drug cartridge carried at the forward end of the device body and having a cylinder in which a piston is movable to cooperatively define a variable-volume chamber holding a dose of liquid medication; a fine-dimension injection orifice in liquid flow communication with the variable-volume chamber to receive the liquid medication and discharge this medication as a high velocity forceful jet for jet injection of the medication upon forceful movement of the piston in the cylinder; a power source in the device body for forcefully moving the piston in the cylinder in response to triggering of the injection device, and a trigger assembly for initiating forceful movement of the piston, the trigger assembly including a trigger pad outwardly disposed on the device body proximate to the forward end and so configured and disposed as to be activated by a user's thumb.

According to a further aspect this invention provides: a method of operating an ergonomic needle-less jet injection device, the device using an injection cartridge having a cylinder receiving liquid medication, an orifice in liquid-flow communication with the cartridge for forming the liquid medication into a high-velocity injection jet, a plug member in a "storage" configuration of the device sealingly separating the liquid medication from the orifice, and an injection piston movable sealingly in the cylinder to displace the liquid medication via the orifice; the method including steps of: providing the device with a two-piece body having a first body portion defining a first bore into which is received a gas-power piston, and a second body portion defining a second bore into which is sealingly and movably received a hermetically sealed pressurized gas capsule; utilizing the first and second body portions and the gas-power piston to cooperatively define a variable-volume chamber; first relatively moving the first and second body portions from the "storage" relative position to an "inject" relative position to forcefully move the plug member from the second bore to provide for open liquid communication from the cartridge to the orifice; providing a pivotally movable thumb pad trigger which is movable from a first position radially inwardly to a second position on the body to effect triggering of the device; and providing a safety feature on the body which in a "safe" position prevents triggering of the device.

Additional objects and advantages of this invention will appear from a reading of the following detailed description of a single exemplary preferred embodiment, taken in conjunction with the appended drawing Figures, in which the same reference numeral is used throughout the several views to indicate the same feature, or features which are analogous in structure or function.

BRIEF DESCRIPTION OF THE DRAWINGS FIGURES

FIG. 1 provides an exterior side elevation view of a single-use, needle-less jet injector device embodying the present invention, and in which the device is in a "storage" configuration;

FIG. 2 is an exterior side elevation view of the injector device seen in FIG. 1, but with the device shown in an "inject" configuration preparatory to effecting a jet injection;

FIG. 3 provides a longitudinal cross sectional view through the needle-less jet injection device of FIG. 1, and shows the device in the "storage" configuration;

FIG. 4 is a fragmentary cross sectional view similar to FIG. 3, but shows the jet injection device in the "inject" configuration;

FIG. 5 is also a fragmentary cross sectional similar to FIGS. 3 and 4, but shows the jet injection device during the process of effecting ajet injection;

FIG. 6 is a fragmentary cross sectional view similar to a portion of FIG. 4, but shows a respective portion of an alternative embodiment of a single-use, needle-less jet injection device according to the present invention;

Figure 7:
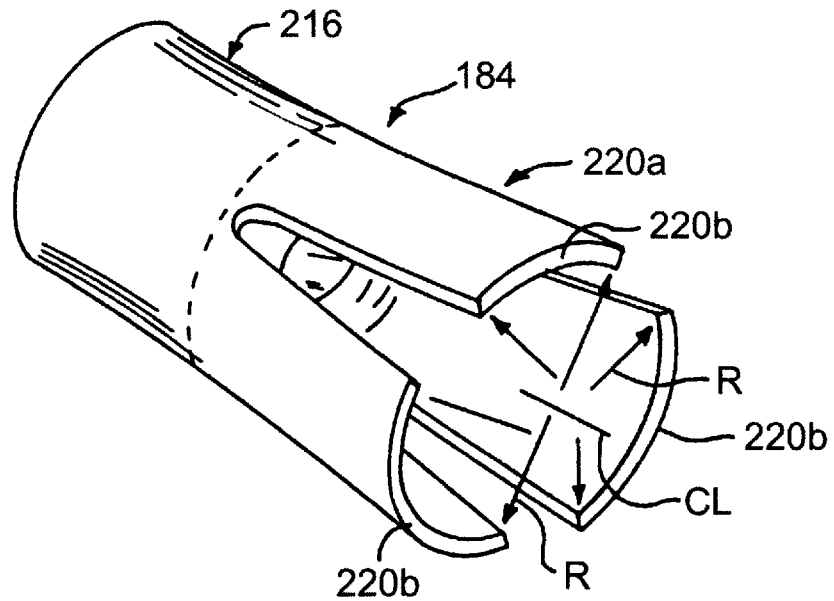
FIG. 7 is a perspective view of a portion of the device seen in FIG. 6.
Figure 8:
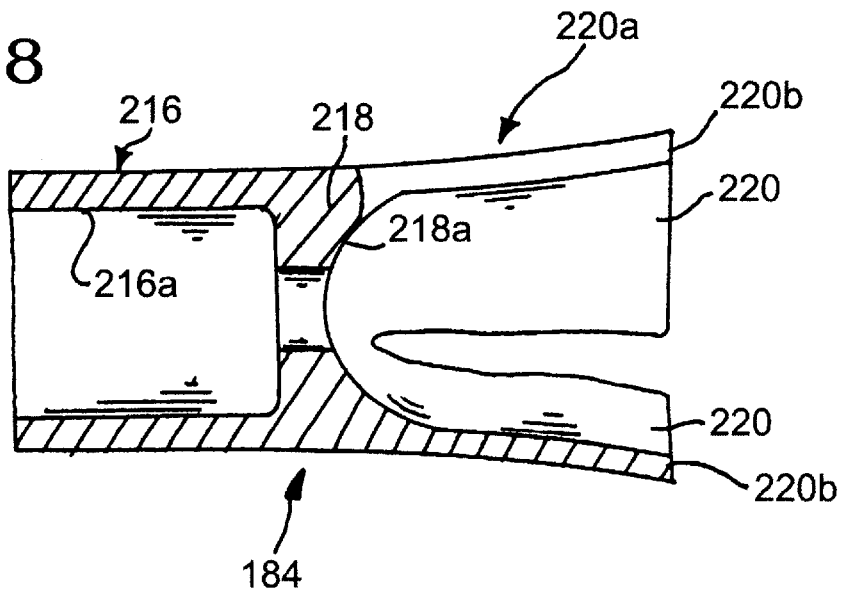
Figure 9:
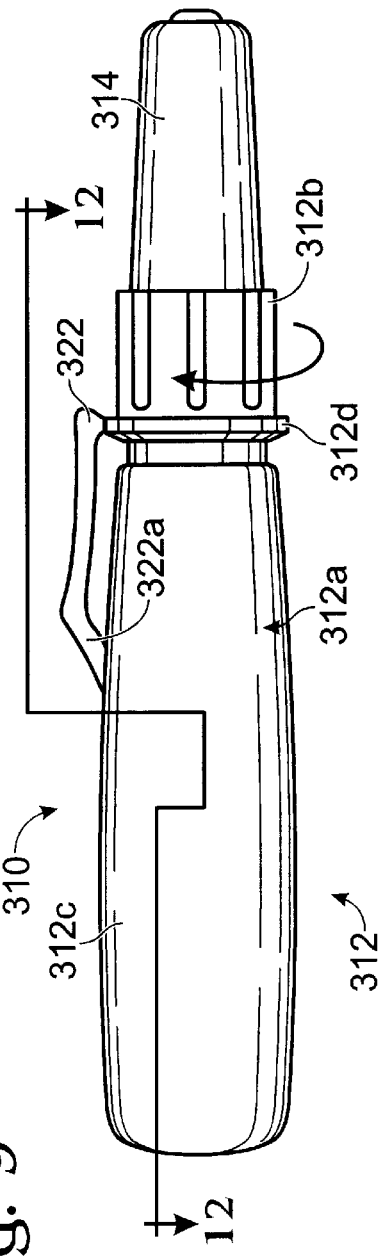
Figure 10:
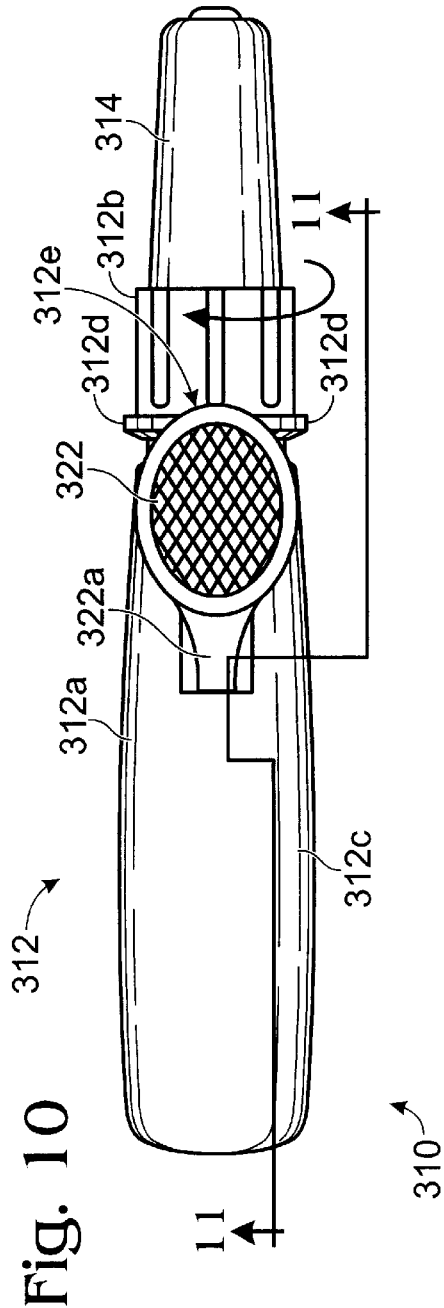
Figure 13:
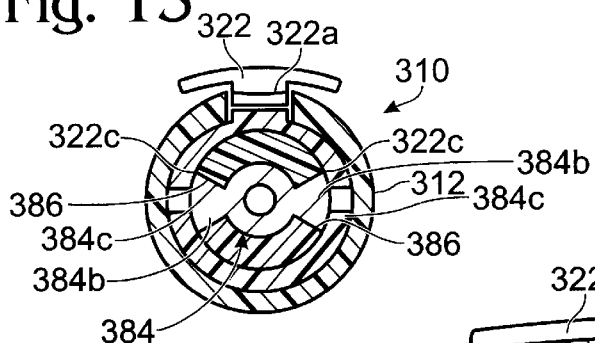
Figure 14:
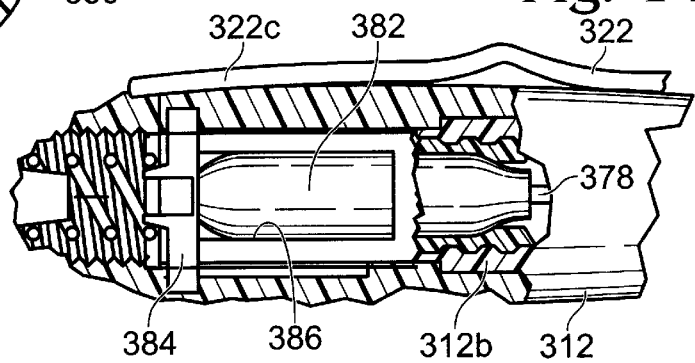
Figure 16:
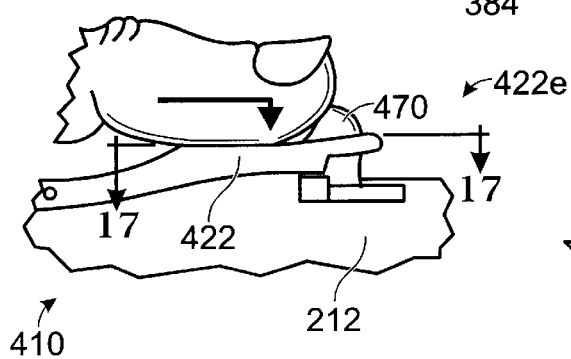
Figure 15:
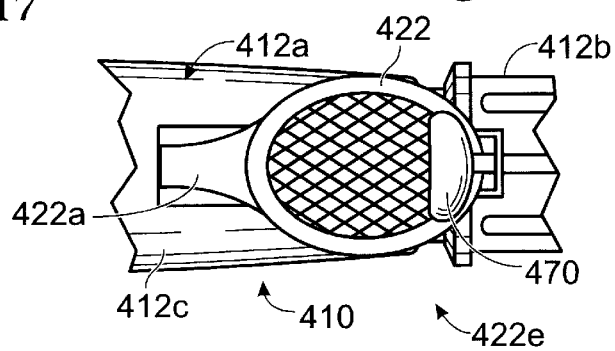
Figure 17:
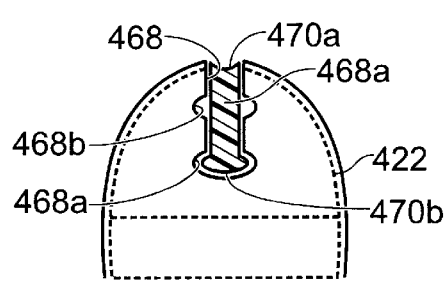

FIG. 8 provides a cross sectional view of the portion of the device seen in FIG. 7;

FIG. 9 provides an exterior side elevation view of an alternative embodiment of a single-use, needle-less jet injector device embodying the present invention, and in which the device is in a "storage" configuration;

FIG. 10 provides an exterior plan view of the device seen in FIG. 9;

FIG. 11 is a fragmentary longitudinal cross sectional view taken generally along line 11—11 of FIG. 10, and looking in the direction of the arrows, but with the device shown in an "inject" configuration preparatory to effecting a jet injection;

FIG. 12 is a fragmentary longitudinal cross sectional view similar to FIG. 11, and taken generally along line 12—12 of FIG. 9, and like FIG. 11 also now shows the jet injection device in the "inject" configuration;

FIG. 13 provides a cross sectional view taken generally at line 13—13 of FIG. 11;

FIG. 14 is a fragmentary cross sectional view similar to a portion of FIG. 11, but showing the device after "triggering", and during the process of effecting a jet injection;

FIG. 15 is a fragmentary plan view similar to FIG. 10, but showing an alternative embodiment of a device embodying the present invention;

FIG. 16 is a fragmentary elevation view of the device seen in FIG. 15, and illustrates preparation for "triggering" of the device and ajet injection; and FIG. 17 is a fragmentary cross sectional view taken generally at line 17—17 of FIG. 16, and illustrates a detent mechanism of the device.

DETAILED DESCRIPTION OF EXEMPLARY PREFERRED EMBODIMENTS OF THE INVENTION

Figure 1:
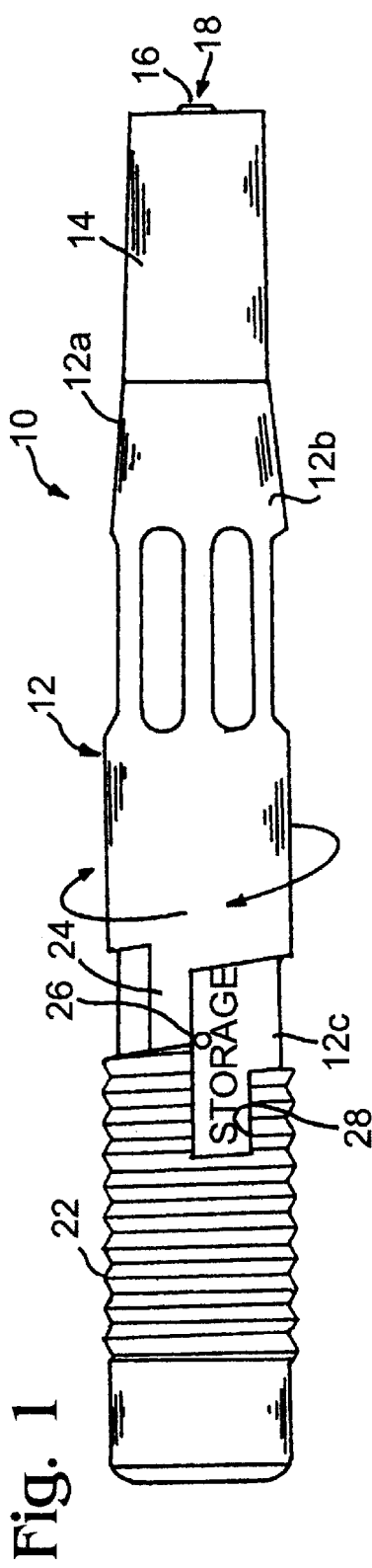

Overview, Storage of the Device, and its Preparation for Effecting a jet Injection Viewing FIG. 1, a needle-free, jet injection device 10 is shown in a storage configuration in which it is maintained until it is prepared for its use in administering an injection. In this storage configuration, the device is incapable of effecting a jet injection, is safe, and can be stored for a comparatively long time while requiring only a moment of preparation before it can be used to make ajet injection of the medication within the device 10.

The device 10 includes a hand piece assembly 12, preferably fabricated principally of injection molded plastic polymers, and with a body 12a including a pre-filled drug injection cartridge 14. The word "drug" as used herein is intended to encompass, for example, and without limitation, any medication, pharmaceutical, therapeutic, vaccine, or other material which can be administered by jet injection. Essentially, such an injectable medication is in the form of a substantially incompressible liquid, and as will be seen, this liquid substantially fills the drug injection cartridge so that no ullage volume of compressible gas is present in this cartridge.

The pre-filled drug injection cartridge 14 has an end surface 16 at which is defined a fine-dimension injection orifice opening 18. When the device 10 is used to effect an injection, a high velocity jet of liquid medication issues from this orifice (as is indicated by arrow 20 of FIG. 5). To use the device 10, it is first placed in an "inject" configuration, the end surface 16 is pressed against the skin of a patient who is to receive the jet injection, and then the device 10 is triggered so that the jet 20 issues out and penetrates the skin. Thus, the liquid medication enters the tissues of the patient without the use of a hypodermic needle.

Placing the device 10 in the "inject" configuration is effected manually by a user of the device 10 who rotates a first portion 12b of the body 12a relative to a second portion 12c. As is seen in FIG. 1, the body portion 12c carries a trigger sleeve 22, while the portion 12b carries a projection 24 abutting this sleeve. The projection 24 and a blocking pin 26 cooperate to prevent the body portions 12b and 12c from being relatively rotated except in the direction of the arrow of FIG. 1. When a user effects this relative rotation of the body portions 12b and 12c through a rotation of almost 360°, then this relative rotation aligns the projection 24 with a recess 28 on the trigger sleeve 22, reveals the abbreviation of the word "inject" (indicated on FIG. 2 by the letters "INJ") on the body portion 12c.

This relative rotation of the body portions 12b and 12c also effects a selected relative axial movement of these body portions toward one another (as will be further described below), and places the device 10 in the "inject" configuration seen in FIG. 2. In this "inject" configuration, the device 10 is positioned with its surface 16 against the skin of the person who is to receive the injection, and an axial pressure is applied to the trigger sleeve 22. The trigger sleeve 22 moves axially along the body portion 12c, and this movement triggers the device 10 to effect injection jet 20 (recalling FIG. 5).

Structure of the Device 10

Turning now to FIGS. 3, 4, and 5, in conjunction with one another, FIG. 3 shows the device 10 in the storage configuration of FIG. 1 preparatory to giving an injection. In FIG. 4 shows the device in the "inject" configuration, and FIG. 5 shows the device during the brief interval of an injection. In these Figures, it is seen that the drug cartridge 14 includes a cylindrical body 30 defining an external thread section 32. This external thread 32 is threadably received by a matching internal thread section 34 of the body portion 12b. Preferably, a thread locking compound, such as an anaerobic adhesive, is applied to the threads 32 of the cartridge 14 when it is assembled to the body portion 12b during manufacture of the device 10. Alternatively, a self-locking thread design or a thread-locking feature may be used on the device 10 to prevent the drug injection cartridge 14 from being removed from the device 10. Thus, the cartridge is not removable from the device 10, and the device 10 and cartridge 14 are disposed of after the first and only injection effected with the device 10.

An advantageous feature of the device 10 embodying the present invention, and one which results from this construction of the device, is that the injection cartridge 14 may be manufactured and filled at a drug company (without the drug manufacture having to be concerned with handling capsules of pressurized gas), the gas pressure capsule of the device may be manufactured and filled at a factory devoted to this item (without this manufacturer having to handle drugs), and the hand piece assembly of the device may be manufactured at yet another location, if desired. Subsequently, completion of the device 10 requires merely the combining of the hand piece assembly, gas capsule, and drug injection cartridge.

The body 30 of cartridge 14 defines a stepped through bore 36 having a larger diameter portion 36a which extends substantially the length of the body 30. Adjacent to the forward end of the body 30 (i.e., adjacent to the end defining surface 16), the bore 36 steps down and defines an outlet orifice 36b. It is seen that the bore portion 36a and outlet orifice 36b are defined by a glass sleeve 38 which is received into a molded plastic body 40. An O-ring type of seal member 42 prevents leakage between the glass sleeve 38 and the body 40.

As those who are ordinarily skilled in the pertinent arts will understand, many medications are not suitable for long-term storage in contact with plastics, but will store satisfactorily in contact with glass. Thus, this construction of the cartridge 14 makes it suitable for long-term storage of even medications of this nature. However, for medications that will store satisfactorily in contact with plastic polymers, this construction detail is optional and the entire injection cartridge body 30 may be formed of a selected polymer.

In the embodiment of cartridge 14 having the glass sleeve 38, the outlet orifice 36b is sealingly closed in the storage configuration of the device 10 by a plug 44. Importantly, viewing FIGS. 3–5, it is seen that the cartridge 14 defines a plug-capture chamber 46 immediately outside of the outlet orifice 36b (i.e., rightwardly of this outlet orifice, viewing FIGS. 3–5). The plug capture chamber 46 includes a radial array 46a of individual radially inwardly and axially extending ribs 48 disposed in a spaced relation to the outlet orifice 36b. These ribs 48 are arrayed radially about and in a transition bore portion 18a leading to the injection orifice 18. Thus, as will be seen, the plug member 44 can be received into the plug-capture chamber 46 and be supported on the ribs 48 without it blocking the injection orifice 18.

Sealingly and movably received in the bore section 36a is a resilient piston member 50. This piston member defines multiple circumferential grooves 50a interdigitated with sealing ribs 50b. The sealing ribs 50b sealingly and movingly engage the bore 36a of the injection cartridge (i.e., with the bore 36a of glass sleeve 38 in this case). The piston member 34 and body 30 cooperatively define a medication chamber 52 communicating outwardly of the cartridge 14 via the injection orifice 18. Prior to its use to effect an injection, the orifice 18 of each fresh and pre-filled device 10 will ordinarily also be sealed by an adhesively-applied, peel-off type of sealing membrane, which may be formed, for example, of foil or of a polymer/paper laminate. Such peel-off seals are conventional and well known, and for this reason, the seal formerly on cartridge 14 of device 10 as seen in FIG. 3 is not shown in the drawings Figures.

Further considering the cartridge 14, it is seen that the piston member 50 defines an abutment surface 54 confronting the opening of bore 36 on body 30. This surface 54 is abutted by an end surface 56 on an injection ram of the hand piece assembly 12 (which injection ram will be further described below). In the storage configuration of the device 10, the end surface 56 confronts piston 50, but does not displace it from the position seen in FIG. 3. In this storage configuration of the device 10, the chamber 52 is sealed and is substantially full of incompressible liquid, without any substantial ullage volume of compressible gas being in the chamber 52. The injection ram will be understood as effective during ajet injection to forcefully move the piston 50 inwardly of the bore section 36a toward the outlet orifice 36b

Hand Piece Assembly 12

Considering now the hand piece assembly 12 in greater detail, as seen in FIGS. 1–5, it is seen that the body 12a generally is formed of two main cooperative tubular sections 12b and 12c, which are threadably engaged with one another to form the hand piece assembly 12. Preferably both of the body sections 12b and 12c, as well as other components of the device 12 not otherwise identified as being made of some other material, are all formed of plastic polymers. Further, the preferred process for making the device 10 is by injection molding of the components formed of plastic polymer, so that manufacturing costs are very low. Materials utilization for the device 10 is very small as well, so that disposing of the device after a single injection does not cause a serious environmental concern.

The forward tubular body section 12b defines a stepped through bore 58, a forward portion 58a of which opens forwardly on the body 12, and which inwardly of this bore opening 58a defines the internal thread section 34 for threadably receiving the external threads 32 on the drug cartridge 14. Sealingly and movably received in the bore portion 58a is a stepped injection piston member 60. A larger diameter portion 60a of this piston member defines a groove 60b carrying a seal member 60c. The seal member 60c movingly engages sealingly with the bore portion 58a and bounds a gas pressure chamber 60d, which is to the left of this piston member as seen in FIGS. 3, 4, and 5. It is to be noted that in FIGS. 3 and 4, this chamber 60d is at a minimal volume, and so the lead line from reference numeral 60d extends into the interface of the piston member 60 with the housing portion 12c.

A smaller diameter portion 60e of the piston member 60 is elongate and extends in the bore 58 to also be received into the bore portion 36a of the drug cartridge 14, as is seen in FIG. 3 in the storage configuration of the device 10. The piston portion 60e defines the end surface 56 which confronts and abuts the surface 54 of the piston member 50 of drug cartridge 14. Thus, the piston portion 60e provides the injection ram of the device 10.

Considering the forward body section 12b in still greater detail, it is seen that this body section defines a tubular aft body section 62. This aft body section includes an axially disposed end surface 62a at which the stepped through bore 58 opens, and which defines an internal thread section 64 threadably engaging onto matching threads 66 of body section 12c. For purposes of explanation, and without limitation of the present invention, the threads 64 and 66 may have a pitch of about 14 threads per inch.

Figure 2:
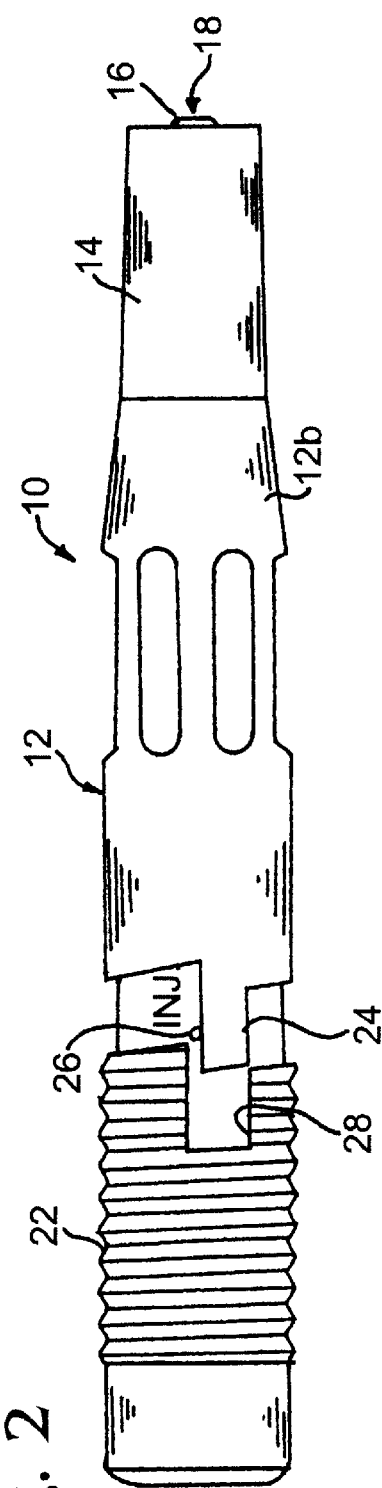

As is seen comparing FIGS. 1 and 2, the device 10 is converted from its storage to its "inject" configuration by rotating the body portions 12b and 12c in a relative rotational direction that threads these body portions together along threads 64 and 66. As was explained above, this relative rotation of the body sections 12b and 12c brings projection 24 into alignment with recess 28 on trigger sleeve 22, and makes possible the subsequent triggering of the device 10. Still considering FIGS. 2 and 3, it is seen that the aft body portion 12c outwardly defines the thread section 66 and slidably carries the trigger sleeve 22. Adjacent to the thread section 66, the body portion 12c carries an O-ring type of sealing member 68 which sealingly engages the body portion 12b both when the body portions are in their "storage" relative configuration of FIG. 3, and also when these body portions are in their "inject" relative positions as is seen in FIGS. 4 and 5.

Body portion 12c defines a stepped through bore 70 which is substantially closed at the end of this bore adjacent to the forward body portion 12b by a wall member 72. This wall member 72 defines a stepped through bore 74 in a larger diameter part of which is seated a disk part 76 of a penetrator member 78. This penetrator member 78 includes a hollow penetrator spike 80 which itself has a bore 80a communicating through the wall member 72 via the smaller diameter portion of bore 74. Thus, the bore 70 is communicated to the chamber 60d adjacent to injection piston 60 in the body portion 12b.

Slidably received in the bore 74 adjacent to and confronting the penetrator member 78 is a gas pressure capsule 82. This gas pressure capsule 82 includes a body 82a, having a cylindrical outer wall portion 82a'. The capsule 82 is also necked down at a forward end to provide a reduced diameter portion 82b leading to an axially disposed end surface 82c defined by a penetrable wall section 82d (the wall section being indicated by the arrowed numeral in FIG. 3). The gas capsule 82 is preferably formed of metal, and contains a supply of pressurized gas. Because the pressurized gas is contained in the capsule 82 until the moment of injection, the plastic parts of the device 10 are not exposed to or stressed by this pressurized gas until an injection is effected using the device 10. For this reason, the device 10 is believed to have a much more reliable storage life then prior devices which attempt to contain pressurized gas in a plastic or plastic-composite containment.

The wall section 82d confronts and is spaced slightly from the penetrator spike 80. At an opposite or aft end of the capsule 82, this capsule defines an outwardly rounded end wall 82e.

Also slidably received into the bore 70 and confronting the end 82e of capsule 82 is tubular and cylindrical hammer member 84. This hammer member 84 defines an end surface 84a which is engageable with the surface 82e of capsule 82, an axially extending groove 86 having an end wall at 86a (into which a dowel pin 88 is received), and an axial protrusion at 90 which serves to center a spring 92.

The dowel pin 88 is engaged in a first position (i.e., in the "storage" configuration of the device 10) at end 86a of groove 86, and the other end of this pin rests upon a metal (i.e., preferably hardened steel) sear pin 94 carried by the body portion 12c. Thus, as is seen in FIGS. 3 and 4, the hammer 84 is maintained in a "cocked" position with the spring 92 pre-loaded between the hammer 84 and a spring seat member 96 threadably engaging into the end of body portion 12c.

In order to provide for movement of the trigger sleeve 22 to effect release of the hammer 84, the body portion 12c defines an axially extending slot 100, and the trigger sleeve 22 carries a radially inwardly extending trigger block 22a, which is slidably received in this slot 100 and which confronts the dowel pin 88, as is seen in FIG. 3. Also, an end cap 102 is adhesively retained onto the trigger sleeve 22 and closes the end of this trigger sleeve so that a user's thumb, for example, may be used to effect forward movement of the trigger sleeve when an injection is to be effected. It will be understood that the trigger sleeve 22 may alternatively be grasped between the thumb and fingers, for example, to position the device 10 for making an injection, and then effecting forward movement of the trigger sleeve 22 to effect this injection.

However, as was pointed out above in connection to the comparison of FIGS. 1 and 2, the device 10 is first placed by a user into its "inject" configuration before a jet injection can be effected. This conversion of the device 10 from its "storage" configuration to its inject configuration is effected by relative rotation of the body portions 12b and 12c, as is indicated by the arrow on FIG. 1. As is seen in FIG. 2, this relative rotation of the body portions 12b and 12c brings the projection 24 into engagement with blocking pin 26 and into alignment with recess 28, so that the trigger sleeve 22 is movable in the axial direction toward body portion 12b. However, viewing FIG. 4, it is seen that this relative rotation of the body portions 12b and 12c also threads body portion 12c by substantially one thread pitch dimension into the body portion 12b.

Because the body portion 12c and wall member 72 are abutting injection piston member 50, this piston member 50 is moved rightwardly, viewing FIG. 4, by substantially one thread pitch dimension. Consequently, the ram portion 60e of the injection piston 60 moves forward and forces piston 50 forwardly by a sufficient amount that plug member 44 is dislodged hydraulically (recalling that the liquid medication in chamber 52 is substantially incompressible) from the outlet orifice 36b and into plug-capture chamber 46. In this chamber 46, the plug member 44 is retained and rests upon the ribs 48 while these rib provide a flow path leading around the plug member 44 from the outlet orifice 36b to the injection orifice 18.

Although the conversion of device 10 from its "storage" configuration to its "inject" configuration unseals the injection cartridge 14, this is not detrimental to the integrity of the medication in chamber 52 because it happens mere moments before the device 10 is used to inject the medication into a patient. This injection is effected by placement of the device 10 with its surface 16 against the skin at the intended location of injection, and sliding of trigger sleeve 22 forward (which also assists in seeing that the device 10 is held firmly to the skin), so that the trigger block 102 slides along slot 100 to dislodge the dowel pin 88 from sear pin 94, viewing FIG. 5.

As is seen in FIG. 5, the result is that the hammer member 84 is driven forward by spring 92, impacts the capsule 82, and impales this capsule at penetrable wall 82d, as is seen in FIG. 5. The result is the penetrator spike 80 penetrates the wall 82c of the capsule 82, and allows pressurized gas from this capsule to flow along the bores 80a and 74 into the chamber 60d. This pressurized gas in chamber 60d drives piston member 60 forwardly, so that the piston 50 in bore 36a is also driven forwardly. Forward movement of piston 50 drives the liquid medication out of chamber 52, past the plug member 44 in plug-capture chamber 46, and out of injection orifice 18, forming injection jet 20.

After the jet injection depicted in FIG. 5, the device 10 is disposed of by the user of the device, and it is not again used. That is, the device 10 is a single-use device and is not designed or intended to be recharged or refilled. This design of the device 10 insures safety for those receiving an injection by use of the device 10 because they can be sure that only a new and never before used device is used to give them the injection. Further, the device 10 provides for long-term storage of the device and its pre-filled medication, so that devices 10 may be stockpiled in anticipation of such events as mass inoculations. The device 10 may be used under exigent circumstances as well, since it requires only a few seconds or less to convert it from its "storage" configuration to its "inject" configuration, after which the jet injection is immediately effected.

FIG. 6 provides a fragmentary view of an alternative embodiment of the jet injection device according to this invention. In FIG. 6, only the aft or trigger assembly end of the device is illustrated. The forward end of the device and its pre-filled medication injection cartridge may be substantially as depicted and described above. Because the device illustrated in FIGS. 6–8 has many features that are the same as, or which are analogous in structure or function to those illustrated and described above, these features are indicated on FIGS. 6–8 using the same reference numeral used above, and increased by one-hundred (100).

Viewing FIGS. 6–8 in conjunction with one another, it is seen that the injection device 110 includes a body portion 112c, which is necked to a slightly smaller diameter aft portion at 214. This aft portion defines a plurality of circumferential barbs 214a, and an end cap 202 is received on these barbs and is permanently engaged there by a matching set of inwardly extending barbs 202a. Slidably received in this body portion 112c is a one-piece molded hammer-and-sear member 184.

Preferably, this member 184 is molded of plastic polymer. The hammer-and-sear member 184 is seen in perspective in FIGS. 7 and 8. It is seen that this hammer-and-sear member 184 includes a cylindrical section 216 defining a spring recess 216a, into which the spring 192 is captively received and preloaded to make the device 110 ready for use. A center wall portion 218 of the member 184 provides a surface 218a, which is engageable with the gas capsule 182 to move this capsule forward, and to impale the capsule on the penetrator spike (not seen in FIG. 6, but recalling FIGS. 3–5 above). In order to hold the hammer-and-sear member against the pre-load of spring 192, and to resist the pressure of this spring over a long term the member 184 includes three axially extending legs 220.

Each of these legs 220 is a portion of a cone-shaped section 220a, best seen in FIGS. 7 and 8. The transition between the circular cylindrical section 216, and the cone-shaped section 220a is indicated with a dashed line circumscribing the member 184 in FIG. 7. Forwardly of this transition, the legs 220 flare out by their own resilience. As is seen in FIG. 6, these legs 220, at an end surface 220b of each one engage upon a ring-like abutment member 222 carried within the body portion 112c. As is best appreciated by consideration of FIG. 7, it is seen that the end surfaces 220b of the legs 220 are not formed on the radius of the cone-shape at this end of the member 184 (i.e., at the cone diameter having a center line indicated as "CL" on FIG. 7), but are formed at a smaller radius corresponding generally with the circular diameter of the section 216 (indicated by the radius lines and character "R" of FIG. 7). During storage of the device 110, these end surfaces 220b rest upon the abutment member 222 and transfer the spring force from spring 192 to this abutment member on a long-term basis.

In order to prevent creep of the plastic polymer material from which the member 184 is formed, the surfaces 220b define cooperatively, a contact area which corresponds substantially to that of the diameter 216 of the member 184 multiplied by the radial thickness of the legs 220.

This contact surface area is sufficient to prevent creeping of the polymer from which the member 184 is formed.

In order to effect release of the hammer-and-sear member 184 when it is desired to effect a jet injection with the device 110, the body portion 112c defines three axially extending slots 200 (only one of which is seen in FIG. 6), each corresponding to a respective one of the legs 220. As is seen in FIG. 6, the trigger sleeve 122 carries three trigger blocks 122a (again, only one of which is seen in FIG. 6) which are slidably received in the slots 200. When this trigger sleeve 122 is moved forward, the trigger blocks 122a simultaneously force respective ones of the legs 220 radially inwardly and out of engagement with the abutment member 222, overcoming both the inherent resilience of these legs and the component of spring force resulting from the radial flaring of these legs. It will be appreciated that in view of this combination of inherent resilience and outward flare of the legs 220, there is virtually no risk that the device 110 will trigger except in response to deliberate forward movement of the trigger sleeve 122.

Because the legs 220 are formed at a circular (rather than conical) radius, they nest together and are received into the ring-like abutment member 222. Thus, the spring 192 forces the hammer-and-sear member 184 forcefully forward, effecting a jet injection from the device 110, as was explained above.

Viewing now FIGS. 9–14, yet another and particularly ergonomic alternative embodiment of a needle-free, jet injection device is shown. Because the device illustrated in FIGS. 9–14 has many features that are the same as, or which are analogous in structure or function to those first illustrated and first described above, these features are indicated on FIGS. 9–14 using the same reference numeral used above, and increased by three-hundred (300). In FIGS. 9, 10 the device is seen in its storage condition, and it will be noted that the device is configured generally to be held somewhat like a tubular flashlight (i.e., pointing forward, perhaps about at waist level, and with the user's thumb on a "trigger" pad of the device). Thus, the device is activated to effect a jet injection in much the same way as a user would turn on such a tubular flashlight. That is, the user employs the thumb to press a "trigger" pad of the device.

FIGS. 9 and 10 show the exterior of the device 310. Viewing FIGS. 9 and 10 in conjunction with one another, it is seen that the device 310 includes a handpiece assembly 312 with a body 312a, having a forward portion 312b and a rear portion 312c. The body portion 312b includes a radially outwardly extending circumferential rib 312d (best seen in FIG. 9), and which in the storage configuration of the device is disposed under a trigger pad 322. This "storage" position of the rib 312d prevents the trigger pad 322 from being moved radially inwardly. In FIG. 10 it is seen that the rib 312d defines a circumferentially extending gap 312e.

As can be understood in view of the explanation above, the body portions 312a and 312b are relatively rotated from the storage configuration of the device 310 to the "inject" configuration (as is indicated by the rotation arrow on FIGS. 9 and 10). This relative rotation of the body portions 312a and 312b brings the gap 312e of rib 312d into radial alignment with the trigger pad 322 (as is best seen in FIGS. 11 and 12) so that the trigger pad can be pressed radially inwardly (see the arrow on FIG. 11) to effect a jet injection with the device 310. In view of the explanation above, it will be understood that the body portion 312b also threads a determined distance into the body portion 312a during the relative rotation of the body portions from the "storage" to the "inject" configuration (i.e., sufficiently to prepare the drug injection cartridge 314 to discharge the medication therein—as was explained by reference to a preceding embodiment).

Attention now to FIGS. 11 and 12 shows that the trigger pad 322 is carried by a trigger stem 322a pivotal in the device 310 on a pin 324. Inwardly of the body 312a, the trigger stem 322a defines a bifurcation, indicated by arrowed reference numeral 322b. Thus, the trigger stem 322a defines a pair of spaced apart trigger legs 322c, each defining an end surface 322d, which is crowned in side elevation view (as is best seen in FIG. 11).

Viewing FIGS. 11, 12, and 13 in conjunction with one another, it is seen that the hammer 384 includes a pair of diametrically opposed radially outwardly extending guide portions 384b, each of which are somewhat trapezoidally shaped in axial view (viewing FIG. 13 in particular). These trapezoidal guide portions 384b of the hammer 384 are received slidably in opposed and matchingly shaped slots 386 (one of which is best seen in FIG. 11) defined by a tubular body portion 362. The tubular body portion 362 is axially and rotationally immovable relative to body portion 312c, and is threadably engaged with body portion 312b so that when the body portions 312a and 312b are relatively rotated to convert the device from the "storage" to the "inject" configuration (recalling the description of FIGS. 9 and 10 versus the configuration of FIGS. 11 and 12), then body portion 312b threads a determined distance into the body portion 362. As with the embodiment first described above, this axial relative movement of the body portions 312b and 362 opens the medication cartridge 314 preparatory to the effecting of a jet injection with the device 310.

Radially outwardly of the guide portions 384b, the hammer 384 defines a pair of diametrically opposite and radially outwardly extending hammer lugs 384c, which are engaged by the trigger legs 322c to retain the hammer in the "storage" position until the device 310 is activated (i.e., is triggered to effect a jet injection). As was explained above, and as is illustrated in FIGS. 11 and 12, with the gap 312e aligned with the trigger pad 322, this trigger pad may be pressed radially inwardly by use of the user's thumb. This movement has the effect of pivoting the trigger stem 322 about the pin 324 so that the trigger legs 322c lift upwardly (viewing FIG. 11), and disengage from the hammer lugs 384c. This triggering movement of the trigger pad 322 is not effortless, and the user will feel the movement of the trigger pad in much the same way a user of a firearm feels the trigger move or "creep" before the firearm discharges. Thus, the user will know by feel as the user applies force to the thumb trigger pad that the device is being moved toward discharging a jet injection. As is seen in FIG. 14, the hammer member 384 then drives pressurized gas capsule 382 forwardly to be impaled upon the penetrator 378. As explained in greater detail above with reference to the first-described embodiment, the device 310 then effects a jet injection.

Particularly, it is to be noted that the device 310 is configured to be operated with the user's thumb, and to be held in the hand with the palm upwardly, and the device pointing forwardly, perhaps about at waist level, somewhat in the way a person holds a straight tubular flashlight. This configuration of the device 10 makes it particularly useful for use at about waist level, as a surgeon might use the device at the side of an operating table. Further, the device is configured for one-handed operation, after it has been prepared for effecting an injection. That is, the user may use two hands to convert the device from its "storage" to its "inject" configuration. But, when the device is in its inject" configuration, the user can manipulate the device and effect the injection without having to use more than one hand, and generally using tactile feedback (i.e., the sense of touch). The thumb pad can be accessed by feel, and may also be triggered by feel without looking at the device.

Viewing now FIGS. 15–17, yet another alternative embodiment of the present invention is shown. Because the device illustrated in FIGS. 15–17 has many features that are the same as, or which are analogous in structure or function to those first illustrated and first described above, these features are indicated on FIGS. 15–17 using the same reference numeral used above, and increased by fourhundred (400). The reader will note that in many respects, the device 410 illustrated in FIGS. 15–17 is very similar to that of FIGS. 9–14. However, the device 410 does differ in the configuration of a safety mechanism, generally indicated with the arrowed numeral 422e. In this embodiment the rib 412d is circumferentially continuous, and does not define a gap (i.e., like gap 312e seen in FIGS. 9 and 10 of the previous embodiment). Consequently, when the device 410 is converted from the "storage" to the "inject" configuration by relatively rotating the forward and rear body parts (as has been explained above), the rib 412d comes into longitudinal alignment with the trigger pad (and particularly, into alignment with a projection 470a of this trigger pad), and prevents downward movement of this trigger pad to trigger the device.

However, viewing FIG. 17, it is seen that the trigger pad 422 defines a longitudinally extending slot 468, having a first 468a, and a second 468b enlargement spaced apart along the length of this slot. A safety release button member 470 is slidably and captively received into the slot 468, and defines the projection 470a. The projection 470a includes a depending rib 470b, which is received in one or the other of the enlargements 468a or 468b of the slot 468, depending on whether the device 410 is in a "safe" or "ready" configuration (i.e., both of which are part of the "inject" configuration of the device. In the "safe" configuration of the device 410, the projection 470a of safety button 470 aligns with the rib 412d, and prevents the trigger pad from being pressed inwardly. However, as is seen in FIG. 16, and is illustrated by the cranked arrow on this Figure (i.e., in the user's thumb), the user may sequentially slide the thumb forwardly along the trigger pad 422, to slide the safety button forwardly so that the projection 470a is no longer in alignment with the rib 412b, and then may press the trigger pad 422 downwardly (i.e., radially inwardly of the device 410) to trigger the device. Of course, the sequential thumb movements (i.e., first forwardly along trigger pad 422 to move the safety button 470 forward, followed by pressing the trigger pad inwardly) which indicated in FIG. 17 by the cranked arrow may be separated by an interval of time, thus allowing the user of the device 410 to first convert the device from its "storage" to its "inject" configuration (i.e., using two hands), and then to place the device in the "ready" condition and to trigger the device, all with only one hand, by use of the tactile sense, and without the need to look at the device 410 to confirm its "safe" configuration, or its readiness to effect an injection.

This safety feature of the device 410 allows the user of the device to first reconfigure the device from its "storage" to its "inject" configuration (which requires two hands to relatively rotate the body parts). This conversion of the device to its "inject" configuration will leave it in the "safe" condition because the user has not pushed the safety button 470 forward. Thereafter, the user may with one hand only and without having to look at the device 410 first convert it from "inject-safe" to "inject-ready" by pushing the safety button 470 forward. As the user does push the safety button 470 forward, there is a tactile sensation of resistance, followed by yielding as the rib 470b slides forwardly along slot 468, and then a further stop as the rib 470b is captured in the enlargement 468b. This places the device in the "inject-ready" condition. Thereafter, the user may trigger the device the device with thumb pressure on the pad 422, all by touch using one hand only, and without the need to look at the device.

While the invention has been depicted and described by reference to two particularly preferred embodiments of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

I claim:

1. An ergonomic jet injection device comprising:

an elongate generally cylindrical device body having a forward end;

a drug cartridge carried at the forward end of said device body and having a cylinder in which a piston is movable to cooperatively define a variable-volume chamber holding a dose of liquid medication;

a fine-dimension injection orifice in liquid flow communication with said variable-volume chamber to receive the liquid medication and discharge this medication as a high velocity forceful jet for jet injection of the medication upon forceful movement of said piston in said cylinder;

a power source in said device body for forcefully moving said piston in said cylinder in response to triggering of said injection device, and a trigger assembly for initiating forceful movement of said piston, said trigger assembly including a trigger pad outwardly disposed on the device body proximate to said forward end and so configured and disposed as to be activated by a user's thumb;

wherein said device body includes two portions which are relatively rotational from a "storage" to an "inject" configuration of the device, a rear one of said device body portions carrying said trigger pad, and a forward one of said device body portions including a safety feature preventing activation of said trigger pad while said body portions are in said "storage" relative rotational position.

2. An ergonomic jet injection device comprising:

an elongate generally cylindrical device body having a forward end;

a drug cartridge carried at the forward end of said device body and having a cylinder in which a piston is movable to cooperatively define a variable-volume chamber holding a dose of liquid medication;

a fine-dimension injection orifice in liquid flow communication with said variable-volume chamber to receive the liquid medication and discharge this medication as a high velocity forceful jet for jet injection of the medication upon forceful movement of said piston in said cylinder; forceful jet for jet injction of the medication upon forceful movement of said piston in said cylinder;

a power source in said device body for forcefully moving said piston in said cylinder in response to triggering of said injection device, and a trigger assembly for initiating forceful movement of said piston, said trigger assembly including a trigger pad outwardly disposed on the device body proximate to said forward end and so configured and disposed as to be activated by a user's thumb;

wherein said device body includes two portions which are relatively rotational from a "storage" to an "inject" configuration of the device, a rear one of said device body portions carrying said trigger pad, and a forward one of said device body portions including a safety feature preventing activation of said trigger pad while said body portions are in said "storage" relative rotational position;

wherein said safety feature includes said forward portion of said device body having a radially outwardly extending circumferential rib aligning with said trigger pad in said "storage" configuration of said device.

3. The ergonomic jet injection device of claim 2 wherein said rib defines a circumferential gap, and in response to relative rotation of said body portions from said "storage" to said "inject" relative rotational positions, said gap is moved into radial alignment with said trigger pad.

4. The ergonomic jet injection device of claim 2 wherein said rib is circumferentially continuous, and said trigger pad carries a safety button moveable between a "safe" position and a "ready" position, and safety button including a projection which is said "safe" position confronts said rib, and in said "ready " position, said safety button being moved forward so that said projection is out of alignment with said rib and said trigger pad is movable to activate the device.

5. An ergonomic needle-less jet injection device comprising:
 a pre-filled drug injection cartridge including:
  a medication cylinder having an outflow passage,
  a drug-injection piston in a first position cooperating with said medication cylinder to define a variable-volume chamber of first selected size,
  an injection nozzle,
  a flow path communicating the outflow passage to said injection nozzle,
  a dose of substantially incompressible liquid medication substantially filling said variable-volume chamber at said first size with substantially no ullage volume,
  said drug-injection piston having a second position cooperating with said medication cylinder to define a variable-volume chamber of second selected size smaller than said first selected size;
 a hand piece assembly having a body of generally elongate cylindrical shape and at a forward end holding said drug injection cartridge, said hand piece assembly including a source of pressurized gas, and means for selectively applying force from said pressurized gas to said drug injection piston to move said drug injection piston from said second position to a third position substantially ejecting said dose of liquid medication via said injection nozzle;
 said hand piece assembly including a first body portion holding said drug injection cartridge, and an axially aligned second body portion which is rotational relative to said first body portion;
 a trigger pad pivotally carried on said second body portion and movable radially inwardly between a first and second position to trigger the device;
 wherein said first and second body portions are relatively rotational from a "storage" to an "inject" configuration of the device, said second one of said device body portions carrying said trigger pad, and said first device body portion including a safety feature preventing activation of said trigger pad while said body portions are in said "storage" relative rotational position.

6. An ergonomic needle-less jet injection device comprising:
 a pre-filled drug injection cartridge including:
  a medication cylinder having an outflow passage,
  a drug-injection piston in a first position cooperating with said medication cylinder to define a variable-volume chamber of first selected size,
  an injection nozzle,
  a flow path communicating the outflow passage to said injection nozzle,
  a dose of substantially incompressible liquid medication substantially filling said variable-volume chamber at said first size with substantially no ullage volume,
  said drug-injection piston having a second position cooperating with said medication cylinder to define a variable-volume chamber of second selected size smaller than said first selected size;
 a hand piece assembly having a body of generally elongate cylindrical shape and at a forward end holding said drug injection cartridge, said hand piece assembly including a source of pressurized gas, and means for selectively applying force from said pressurized gas to said drug injection piston to move said drug injection piston from said second position to a third position substantially ejecting said dose of liquid medication via said injection nozzle;
 said hand piece assembly including a first body portion holding said drug injection cartridge, and an axially aligned second body portion which is rotational relative to said first body portion;
 a trigger pad pivotally carried on said second body portion and movable radially inwardly between a first and second position to trigger the device;
 wherein said first and second body portions are relatively rotational from a "storage" to an "inject" configuration of the device, said second one of said device body portions carrying said trigger pad, and said first device body portion including a safety feature preventing activation of said trigger pad while said body portions are in said "storage" relative rotational position;
 wherein said safety feature includes said first portion of said device body having a radially outwardly extending circumferential rib aligning with said trigger pad in said "storage" configuration of said device and preventing said trigger pad from being moved radially inwardly to trigger the device.

7. The ergonomic jet injection device of claim 6 wherein said rib defines a circumferential gap, and in response to relative rotation of said body portions from said "storage" to said "inject" relative rotational positions, said gap is moved into radial alignment with said trigger pad, whereby when said trigger pad is aligned with said gap the trigger pad can be pressed radially inwardly sufficiently to effect triggering of the device.

8. The ergonomic jet injection device of claim 6 wherein said safety feature includes said rib being circumferentially continuous, and said trigger pad carries a safety button movable between a "safe" position and a "ready" position, said safety button including a projection which in said "safe" position confronts said rib and prevents said trigger pad from being moved inwardly sufficiently to trigger the device, and in said "ready" position said safety button being moved forward so that said projection is out of alignment with said rib and said trigger pad is movable radially inwardly sufficiently to trigger the device.

9. An ergonomic needle-less jet injection device especially configured to provide tactile inputs to a user indicative of the configuration and status of the device, said device comprising:
 a body assembly substantially formed of plastic polymer, said body assembly being of generally elongate cylindrical shape with a forward end;

a jet injection cartridge carried by said body at said forward end, said injection cartridge receiving a dose of liquid medication which is forcefully ejected when the device is triggered, and a fine-dimension jet injection orifice in liquid flow communication with said dose of liquid medication and via which the liquid medication is effected as a high velocity injection jet when the device is triggered;

a metallic pre-filled hermetically-sealed single-use gas pressure cartridge disposed in said body, said gas pressure cartridge having a penetrable wall portion and said body including a penetrator for penetrating said penetrable wall portion of said gas cartridge and releasing pressurized gas from said cartridge;

said device further including means responsive to pressurized gas released from said gas pressure cartridge for applying force to said liquid medication to eject said medication via said jet injection orifice;

said device further including means for selectively impaling said gas pressure cartridge at said penetrable wall portion upon said penetrator to effect a jet injection in response to triggering of the device; and a trigger pad outwardly disposed on said device body and movable radially inwardly in response to thumb pressure to effect triggering of the device, wherein said device body includes relatively rotational first and second body portions, said first and said second body portions being relatively rotational from "storage" to an "inject" configuration of the device, said first body portions carrying said drug injection cartridge, and said second device body portion carrying said trigger pad.

10. An ergonomic needle-less jet injection device especially configured to provide tactile inputs to a user indicative of the configuration and status of the device, said device comprising:

a body assembly substantially formed of plastic polymer, said body assembly being of generally elongate cylindrical shape with a forward end;

a jet injection cartridge carried by said body at said forward end, said injection cartridge receiving a dose of liquid medication which is forcefully ejected when the device is triggered, and a fine-dimension jet injection orifice in liquid flow communication with said dose of liquid medication and via which the liquid medication is effected as a high velocity injection jet when the device is triggered;

a metallic pre-filled hermetically-sealed single-use gas pressure cartridge disposed in said body, said gas pressure cartridge having a penetrable wall portion and said body including a penetrator for penetrating said penetrable wall portion of said gas cartridge and releasing pressurized gas from said cartridge;

said device further including means responsive to pressurized gas released from said gas pressure cartridge for applying force to said liquid medication to eject said medication via said jet injection orifice;

said device further including means for selectively impaling said gas pressure cartridge at said penetrable wall portion upon said penetrator to effect a jet injection in response to triggering of the device; and a trigger pad outwardly disposed on said device body and movable radially inwardly in response to thumb pressure to effect triggering of the device, wherein said device body includes relatively rotational first and second body portions, said first and said second body portions being relatively rotational from "storage" to an "inject" configuration of the device, said first body portions carrying said drug injection cartridge, and said second device body portion carrying said trigger pad;

further including a safety feature preventing inward movement of said trigger pad to effect triggering of said device.

11. The ergonomic jet injection device of claim 10 wherein said first portion of said device body has a radially outwardly extending circumferential rib aligning with said trigger pad in said "storage" configuration of said device to prevent said trigger pad from being moved radially inwardly to trigger the device.

12. The ergonomic jet injection device of claim 11 wherein said rib defines a circumferential gap, and in response to relative rotation of said body portions from said "storage" to said "inject" relative rotational positions, said gap is moved into radial alignment with said trigger pad, whereby when said trigger pad is aligned with said gap the trigger pad can be pressed radially inwardly sufficiently to effect triggering of the device.

13. The ergonomic jet injection device of claim 10 wherein said safety feature includes said first body portion including a radially outwardly extending rib which is circumferentially continuous, and said trigger pad carries a safety button movable between a "safe" position and a "ready" position, said safety button including a projection which in said "safe" position confronts said rib and prevents said trigger pad from being moved inwardly sufficiently to trigger the device, and in said "ready" position said safety button being moved forward so that said projection is out of alignment with said rib and said trigger pad is movable radially inwardly sufficiently to trigger the device.

14. The ergonomic jet injection device of claim 10 wherein said gas pressure cartridge contains nitrogen gas.

15. An ergonomic needle-less jet injection device comprising:

a pre-filled drug injection cartridge including: a medication cylinder having an outlet orifice, a plug member sealingly closing the outlet orifice, an injection nozzle, a flow path communicating the outlet orifice to said injection nozzle, a drug-injection piston in a first position cooperating with said medication cylinder to define a variable-volume chamber of first selected size, a dose of substantially incompressible liquid medication substantially filling said variable-volume chamber at said first size with substantially no ullage volume, said drug-injection piston having a second position cooperating with said medication cylinder to define a variable-volume chamber of second selected size sufficiently smaller than said first selected size that said plug member is hydraulically forced from said outlet orifice;

a hand piece assembly having a generally cylindrical elongate two-piece body having a first body portion holding said drug injection cartridge, and a second body portion providing an abutment movable relative to said first body portion to move said drug injection piston between said first and second positions;

a source of pressurized gas including a hermetically sealed metallic gas capsule;

trigger means for selectively penetrating said gas capsule and for applying force from said pressurized gas to said drug injection piston to move said drug injection piston from said second position to a third position substantially ejecting said dose of liquid medication via said injection nozzle, said trigger means including a thumb pad trigger pivotally carried upon said second body portion.

16. The ergonomic jet injection device of claim 15, wherein said first body portion defines a first bore, a gas-power piston movably received in said first bore, said gas-power piston having a piston head and a ram portion extending into said drug injection cartridge to abut with said drug-injection piston, said first body portion and said gas-power piston cooperating to define a first variable-volume gas-power chamber in said first bore;
said second body portion sealingly and movably engaging with said first body portion to bound said gas-power chamber, said second body portion defining an elongate second bore in gas flow communication with said gas-power chamber, and said gas capsule being received into said second bore.

17. The ergonomic jet injection device of claim 16 wherein said first body portion and said second body portion are threadably and adjustably engaged with one another, said second body portion including said abutment on a wall portion separating said second bore from said gas-power chamber.

18. A method of operating an ergonomic needle-less jet injection device, said device using an injection cartridge having a cylinder receiving liquid medication, an orifice in liquid-flow communication with the cartridge for forming the liquid medication into a high-velocity injection jet, a plug member in a "storage" configuration of the device sealingly separating said liquid medication from said orifice, and an injection piston movable sealingly in said cylinder to displace said liquid medication via said orifice; said method including steps of:
providing said device with a two-piece body having a first body portion defining a first bore into which is received a gas-power piston, and a second body portion defining a second bore into which is sealingly and movably received a hermetically sealed pressurized gas capsule; utilizing said first and second body portions and said gas-power piston to cooperatively define a variable-volume chamber;
first relatively moving said first and second body portions from said "storage" relative position to an "inject" relative position to forcefully move said plug member from said second bore to provide for open liquid communication from said cartridge to said orifice;
providing a pivotally movable thumb pad trigger which is movable from a first position radially inwardly to a second position on said body to effect triggering of the device; and
providing a safety feature on said body which in a "safe" position prevents triggering of the device.

19. The method of operating a needle-less injection device of claim 18 further including the step of relatively moving said first and second body portions of said device body by relatively rotational from a "storage" to an "inject" configuration of the device, providing for a rear one of said device body portions to carry said trigger pad, and providing for a forward one of said device body portions include said safety feature preventing activation of said trigger pad while said body portions are in said "storage" relative rotational position.

20. A method of operating an ergonomic needle-less jet injection device, said device using an injection cartridge having a cylinder receiving liquid medication, an orifice in liquid-flow communication with the cartridge for forming the liquid medication into a high-velocity injection jet, a plug member in a "storage" configuration of the device sealingly separating said liquid medication from said orifice, and an injection piston movable sealingly in said cylinder to displace said liquid medication via said orifice; said method including steps of:
providing said device with a two-piece body having a first body portion defining a first bore into which is received a gas-power piston, and a second body portion defining a second bore into which is sealingly and movably received a hermetically sealed pressurized gas capsule; utilizing said first and second body portions and said gas-power piston to cooperatively define a variable-volume chamber;
first relatively moving said first and second body portions from said "storage" relative position to an "inject" relative position to forcefully move said plug member from said second bore to provide for open liquid communication from said cartridge to said orifice;
providing a pivotally movable thumb pad trigger which is movable from a first position radially inwardly to a second position on said body to effect triggering of the device; and
providing a safety feature on said body which in a "safe" position prevents triggering of the device;
further including the step of relatively moving said first and second body portions of said device body by relatively rotational from a "storage" to an "inject" configuration of the device, providing for a rear one of said device body portions to carry said trigger pad, and providing for a forward one of said device body portions include said safety feature preventing activation of said trigger pad while said body portions are in said "storage" relative rotational position;
further including the step of providing said safety feature to include said forward portion of said device body having a radially outwardly extending circumferential rib aligning with said trigger pad in said "storage" configuration of said device.

21. The method of operating an ergonomic jet injection device of claim 20 further including the step of providing said rib with a circumferential gap, and relatively rotating said first and said second body portions from said "storage" to said "inject" relative rotational position in which said gap is moved into radial alignment with said trigger pad and allows the trigger pad to be moved with a user's thumb radially inwardly to effect triggering of the device.

22. The method of operating an ergonomic jet injection device of claim 20 further including the steps of configuring said rib to be circumferentially continuous, and providing said trigger pad with a safety button movable between a "safe" position and a "ready" position, configuring said safety button to include a projection which in said "safe" position confronts said rib to prevent triggering of the device, and configuring said safety button to in said "ready" position to be relatively moved forward so that said projection is out of alignment with said rib and said trigger pad is movable to activate the device.

* * * * *